United States Patent [19]
Cloyd

[11] 3,965,898
[45] June 29, 1976

[54] SYRINGE
[75] Inventor: Harold S. Cloyd, Erie, Pa.
[73] Assignee: Nosco Plastics, Inc., Erie, Pa.
[22] Filed: Feb. 18, 1975
[21] Appl. No.: 550,628

[52] U.S. Cl. ............................................. 128/220
[51] Int. Cl.² ........................................ A61M 5/00
[58] Field of Search ............ 128/220, 221, 218, 215

[56] References Cited
UNITED STATES PATENTS

| | | | |
|---|---|---|---|
| 1,799,463 | 4/1931 | Hein .................................. | 128/220 |
| 3,176,595 | 4/1965 | Schwartz ......................... | 128/218 P |
| 3,766,919 | 10/1973 | Cloyd ................................. | 128/220 |

*Primary Examiner*—John D. Yasko
*Attorney, Agent, or Firm*—Ralph Hammar

[57] ABSTRACT

A syringe using a pre-filled vial as its barrel and the vial stopper as its piston for expelling liquid from the vial. The stopper has a fill opening large enough to serve as a vent during filling and a plug sealed in said opening after filling. The plug has a puncturable diaphragm for establishing communication between the liquid contents of the vial and the needle of the syringe.

9 Claims, 3 Drawing Figures

SYRINGE

This invention is intended to reduce the cost of factory filled syringes by filling a vial, which subsequently becomes the barrel of the syringe, through a stopper, which subsequently becomes the piston of the syringe. The stopper has a fill opening large enough to vent air during the filling. After filling the vial to the desired level, the fill opening is closed by a plug containing a puncturable diaphragm which connects the vial and the needle of the syringe at the time of use. The structure accommodates the usual variations in the level of filling.

Figure 1:
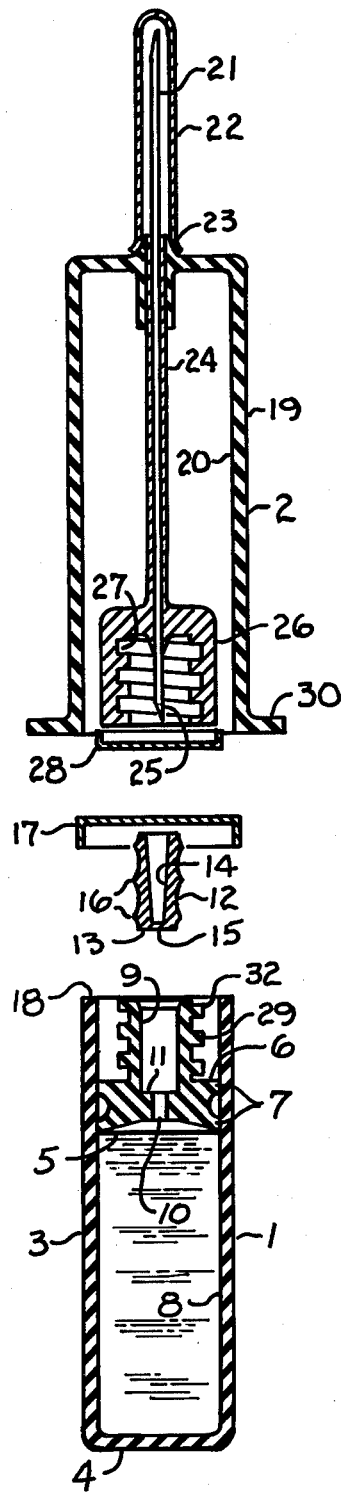
FIG. 1 is an exploded view of a vial and syringe combination.

The syringe of FIG. 1 comprises a vial unit 1 and a needle unit 2. Each unit is separately manufactured and usually is purchased by the ultimate user in sets. The vial unit is factory filled with the desired medicament and the vial and needle units are sterilized and packaged so as to arrive at the point of use in sterile condition. This maximizes the safety to the patient.

The vial 3 is closed at its lower end 4 and is filled to the level 5 with the medicament. In the upper part of the vial is a rubber piston 6 having peropheral ribs 7 in sliding sealing engagement with the inner wall 8 of the vial. At the center of the piston is a bore having a reduced section at its lower end and a shoulder 11. The bore 9, 10 serves as an air vent during the filling operation. In one filling procedure the piston 6 is positioned in an empty vial at the level to which the vial is to be filled. A filling tube of smaller diameter than the reduced section 10 is then inserted through the bore 9, 10 to fill the vial. As the filling progresses, air displaced by the rising liquid level is vented through the clearance between the filling tube and the section 10. After the filling operation is completed a plug 12 is pushed into the bore 9 until a lower end 13 seats on the shoulder 11. The plug has a tapered bore 14 and at its lower end has a puncturable diaphragm 15 closing the lower end of the plug. When pushed in place the puncturable diaphragm 15 is centered on the upper end of the section 10. The tapered bore 14 which converges to a minimum diameter directly above the puncturable diaphragm 15 serves as a guide for the needle. The outside of the plug 12 is provided with ribs 16 which have an outside diameter sufficiently greater than the inside diameter of the bore 9 to make a sealing fit with the bore.

If the vial is filled above the level indicated by the numeral 5 the hydraulic pressure developed by insertion of the plug 12 causes the piston 6 to slide upwardly in the vial and does not prevent the assembly of the plug into the piston. The small amount of air trapped by the insertion of the plug 12 is not objectionable. Before use, liquid is always forced into the needle to expel air. After assembly of the plug a cap 17 is seated on the rim 18 of the vial to exclude dirt. The cap 17 is in the nature of a dust cover.

The needle unit 2 has a cylindrical holder 19 with a bore 20 slidably receivable over the outside of the vial 3. At the upper end of the needle unit is a needle 21 covered by a needle cap 22 seated on a projection 23. The needle may be double ended and molded into a hub 24 with the lower end 25 projecting into a socket 26 having internal threads 27. After manufacture the open end of the socket is closed by a removable cap 28. When the combination is to be used for injection, caps 17 and 28 are removed and the socket 26 is threaded on to a projection 29 at the upper end of the piston 6 having external threads 32 complimentary to the internal threads 27. When socket 26 is screwed onto the projection 29 the lower end 25 of the needle punctures the diaphragm 15 and establishes communication between the needle and the liquid contents of the vial. Liquid is expelled from the vial by moving the vial toward the needle unit which is conveniently done by external pressure on the vial while holding the needle unit by projection 30. The syringe is ready for use after Cap 22 is removed and pressure is applied to the vial to force the liquid into the needle to expel any trapped air from the needle.

The syringe unit 2 is described in greater detail in U.S. Pat. No. 3,766,919 incorporated by reference.

Figure 3:
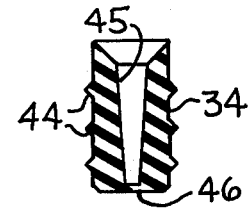
FIGS. 2 and 3 show a modification of the stopper which may be substituted in FIG. 1.
Figure 2:
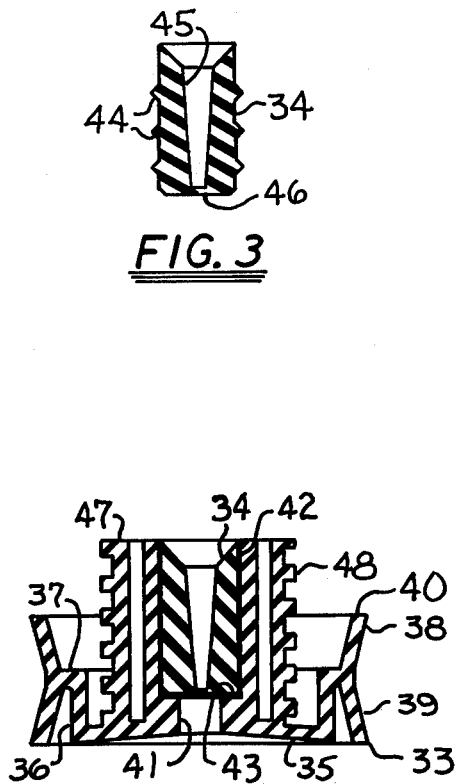

FIGS. 2 and 3 show a modification of the piston adapted to molding from flexible thermoplastics indifferent to the medicament such as polyethylene, polypropylene, etc. The FIG. 2 and 3 construction may be substituted for the piston in the vial unit of FIG. 1. The piston comprises two separately molded parts, a piston member 33 corresponding to the piston 6 in FIG. 1 and a plug 34 corresponding to the plug 12 in FIG. 1. The piston member has a head 35 presented to the liquid in the vial. At the outer periphery of the head is a cylindrical flange 36 extending away from the liquid. Diverging from the upper end 37 of the flange 36 are frustoconical flanges 38, 39 which are stiff enough to make static sealing engagement with the bore 8 of the vial 3. The required stiffness of the flange to produce the static sealing pressure is obtained when the flanges are 0.015 to 0.075 in. thick and when an axial length of 1/8 to 5/32 in. Since sealing pressure is obtained by deflection of the flanges, the outer edges should be blunt and nonfeathered in order that the insertion of the piston into the vial will not result in merely bending the outer edges of the flanges rather than developing sealing pressure.

At the center of the piston head 35 is a bore 41 through which liquid may flow into the end of the vial. On the upper side of the piston is an enlarged bore 42 at the lower end of which is a shoulder on which the plug 34 is seated. Because the plug 34 is made of thermoplastic which does not have the self sealing properties of rubber it is necessary to provide a seal between the plug and the bore 42 and between the plug and the needle. The seal between the plug and the bore 42 is provided by externally projecting sealing ribs 44. The seal between the plug and the needle is provided by a tapered bore 45 which is at its lower end has a diameter about 0.005 in. less than the outside diameter of the needle so that as the needle 25 ruptures the diaphragm 46 at the lower end of the bore 45, a liquid tight seal is obtained between the lower end of the bore 45 and the outside of the needle 25.

The FIG. 3 piston has a cylindrical section 47 provided external threads 48 for mating with the internal threads 27 of the socket 26 of FIG. 1 in the same manner as external threads 32 on projection 29. As the threads 48, 27 are made up, the needle 25 ruptures the diaphragm 46.

When the parts of FIGS. 2 and 3 is substituted for the piston 6, the resultant vial is used in the same manner as the vial shown in FIG. 1. The flanges 38, 39 make the same liquid tight seal as the sealing ribs 7 of the piston 6. The flanges 38, 39 are superior to the sealing ribs 7 in several respects. First, the flanges are more indifferent to medicaments than rubber. Second, the coefficient of friction of thermoplastics is less than rubber. Third, the thermoplastic flanges 38, 39 accommodate greater variations in the inside diameter and out of roundness of the vial.

What is claimed is:

1. A vial having tubular side walls with means for closing one end and with the other end open,
   a piston received in coaxial with the vial having a head presented to the closed end of the vial, a first coupling element presented to the open end of the vial, means on the piston sealing engagement with the side walls of the vial, and an open way of smaller diameter than the piston extending axially through the piston,
   a plug of diameter smaller than the piston received in and closing said way, said plug having means in sealing engagement with said way, a passageway in said plug having one end presented to the open end of the vial and the other end presented to the closed end of the vial, and a diaphragm across and closing said passageway, said passageway having a portion for receiving a needle for puncturing said diaphragm to establish communication between the contents of the vial and the needle.

2. The vial of claim 1 in which the sealing means on the piston comprises annular rubber ribs.

3. The vial of claim 1 in which the needle receiving portion of the passageway converges toward said diaphragm to a diameter less than the diameter of the needle which punctures the diaphragm.

4. The vial of claim 1 in which the sealing means on the piston comprises a plastic flange diverging at an acute angle toward the side wall of the vial.

5. The vial of claim 1 in which a needle holder is in telescoping relation to the vial with the needle inserted in said passageway and has a second coupling element engaging the first coupling element.

6. The vial of claim 5 in which the first coupling element is an externally threaded projection and the second coupling element is an internally threaded socket.

7. The vial of claim 2 in which a needle holder is in telescoping relation to the vial with its needle inserted in said passageway and has a second coupling element engaging the first coupling element.

8. The vial of claim 3 in which a needle holder is in telescoping relation to the vial with its needle inserted in said passageway and has a second coupling element engaging the first coupling element.

9. The vial of claim 4 in which a needle holder is in telescoping relation to the vial with its needle inserted in said passageway and has a second coupling element engaging the first coupling element.

* * * * *